US008680306B2

(12) United States Patent
Chahen et al.

(10) Patent No.: US 8,680,306 B2
(45) Date of Patent: Mar. 25, 2014

(54) COMPLEXES AND METHOD FOR SYNTHESIS OF GROUP 6 ORGANOMETALLICS, AND USE THEREOF IN AN OLEFIN METATHESIS METHOD

(75) Inventors: Ludovic Chahen, Vienne (FR); Mikael Berthod, Lyons (FR); Helene Olivier-Bourbigou, Saint Genis-Laval (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 608 days.

(21) Appl. No.: 12/911,973

(22) Filed: Oct. 26, 2010

(65) Prior Publication Data

US 2011/0098496 A1 Apr. 28, 2011

(30) Foreign Application Priority Data

Oct. 27, 2009 (FR) ...................................... 09 05157

(51) Int. Cl.
 *C07F 5/02* (2006.01)
(52) U.S. Cl.
 USPC .............................................................. 556/7
(58) Field of Classification Search
 None
 See application file for complete search history.

(56) References Cited

U.S. PATENT DOCUMENTS

| 5,405,924 | A | * | 4/1995 | Kelsey .......................... 526/142 |
| 2008/0119678 | A1 | * | 5/2008 | Hock et al. .................... 585/500 |

OTHER PUBLICATIONS

Cole, S., et al. "Transition-metal imido-boroxide complexes: a structural and spectroscopic investigation of the influence of boron," J. Chem. Soc., Dalton Trans., (2002) 4168-4174.*
Gibson, V. et al. "Synthesis and structural characterization of some novel metalloboroxides bearing boron-bound mesityl and fluoromesityl substituents: the molecular structure of the first metalloboroxane complex," Polyhedron, (1997) 16: 2637-2641.*
Search Report of FR 0905157 (Apr. 29, 2010).
A. Jiang et al., "Cationic Molybdenum Imido Alkylidene Complexes," Organometallics, vol. 27, No. 17 pp. 4428-4438.
R. Schrock et al., "Olefin Metathesis by Molybdenum Imido Alkylidene Catalysts," Tetrahedron, vol. 55, No. 27 (1999) pp. 8141-8153.

* cited by examiner

*Primary Examiner* — Sudhakar Katakam
(74) *Attorney, Agent, or Firm* — Millen, White, Zelano & Branigan, P.C.

(57) ABSTRACT

Novel group 6 organometallic compounds are obtained by reaction of at least one boron compound comprising at least one hydroxy, sulfhydryl or amino function with at least one compound of a group 6 transition metal. These compounds are used in a catalytic composition utilized in an olefin metathesis method.

20 Claims, No Drawings

COMPLEXES AND METHOD FOR SYNTHESIS OF GROUP 6 ORGANOMETALLICS, AND USE THEREOF IN AN OLEFIN METATHESIS METHOD

FIELD OF THE INVENTION

The present invention relates to novel group 6 organometallic complexes. It also relates to a method for synthesizing these compounds. It also describes an olefin metathesis method using a catalytic composition utilizing the organometallic complexes according to the present invention.

BACKGROUND OF THE INVENTION

Homogeneous reactions catalysed by transition metals, allowing formation of carbon-carbon bonds, are considered to be important synthetic methods. One example thereof is the olefin metathesis reaction, which has proved its efficiency in the synthesis of high-molecular-weight polymers as well as the synthesis of medicines or other materials. Metal alkylidene complexes, notably molybdenum complexes, have shown good activities in homogeneous olefin metathesis reactions, even in the presence of various functional groups, and these performances greatly depend on the other ligands present around the metal. By way of example, R. R. Schrock's work can be mentioned, who compared the activities of many molybdenum and tungsten imidocarb complexes for the homometathesis of 1-octene (*Organometallics*, 2009, 28 (1), 355-360).

In 2002, Martyn P. Coles' group proved that the $(R_2BO)^-$ and $(RBO_2)^{2-}$ ligands could be coordinated to a metal such as molybdenum (*J. Chem. Soc., Dalton Trans.*, 2002, 4168-4174) or zirconium to form novel complexes (*Inorg. Chem.*, 2002, 41 (13), 3548-3552). These ligands provide steric and electronic effects that are different from their carbon-containing homologs.

We have discovered novel group 6 organometallic complexes having one or more boron-containing ligands bonded to the metal via a heteroatom. These complexes have the specific feature of being active as catalysts in olefin metathesis reactions.

DETAILED DESCRIPTION

The present invention describes organometallic compounds based on a group 6 metal, of imido alkylidene type, comprising at least one boron-based ligand, bonded to the metal via a covalent bond with a heteroatom selected from among sulfur, oxygen or nitrogen.

The organometallic compounds according to the present invention meet one of the following general formulas I, II, III or IV:

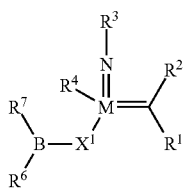

I

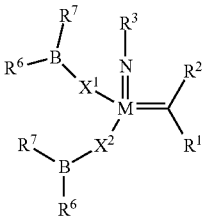

II

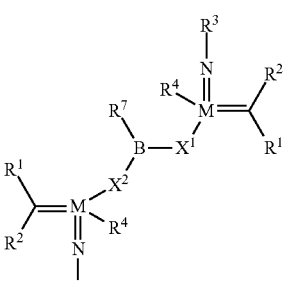

III

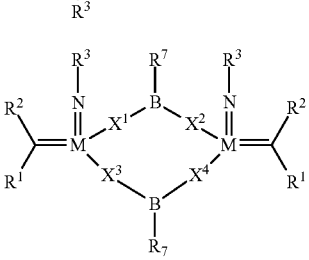

IV wherein:
M represents molybdenum or tungsten,
$X^1$, $X^2$, $X^3$, $X^4$, different or identical, represent an oxygen atom, a sulfur atom or a NH group; optionally substituted by a hydrocarbyl radical having 1 to 30 carbon atoms,
$R^1$, $R^2$, $R^3$ and $R^4$, identical or different, represent hydrogen, halogenides or organic radicals having 1 to 30 carbon atoms,
$R^6$ and $R^7$, identical or different, represent organic radicals having 1 to 30 carbon atoms.

In the aforementioned compounds, groups $R^6$ and $R^7$, identical or different, represent alkyl, cycloalkyl or aromatic, aryl or aralkyl radicals, optionally substituted, hydrocarbyl radicals wherein one or more hydrogen atoms are replaced by halogenides or groups comprising at least one heteroelement selected from the elements oxygen, nitrogen, sulfur or silicon, alkoxy, aryloxy or amidide groups, and groups $R^1$, $R^2$, $R^3$ and $R^4$ represent alkyl, cycloalkyl or aryl groups, optionally substituted, cyclopentadienyls, substituted or not, alkoxy, aryloxy, amidide, hydrido, carboxylate, oxalate, β-diketiminate, iminopyrrolide, amidinate or boratabenzene groups. These products are obtained by reaction of at least one boron compound comprising at least one hydroxy, amino or sulfhydryl function of general formula A or A' with at least one compound of a group 6 transition metal of imido alkylidene type of general formula B.

The present invention also describes a mixture of group 6 organometallic compounds of imido alkylidene type, comprising at least one boron-based ligand, bonded to the metal via a covalent bond with a heteroatom selected from among sulfur, oxygen or nitrogen, obtained by reaction between at least one boron compound comprising at least one hydroxy, amino or sulfhydryl function, of general formula A or A', and at least one compound of a group 6 transition metal of imido alkylidene type, of general formula B, optionally in the presence of a solvent.

The present invention describes a method for synthesis of group 6 organometallic compounds or of the mixture of compounds as defined above obtained by reacting at least one boron compound comprising at least one hydroxy, amino or sulfhydryl function of general formula A or A', optionally activated by a base, with at least one compound of a group 6 transition metal of imido alkylidene type of general formula B, optionally in the presence of a solvent.

The present invention also describes a catalytic composition resulting from contacting:
- at least one boron compound comprising at least one hydroxy, amino or sulfhydryl group of general formula A or A', optionally activated by a base,
- at least one compound of a group 6 transition metal of imido alkylidene type of formula B,
- and optionally a solvent.

The present invention also describes a catalytic composition comprising:
- at least one group 6 organometallic compound meeting one of general formulas I, II, III or IV,
- and optionally a solvent.

The present invention also describes an olefin metathesis method using said catalytic compositions.

The presence of the covalent metal-heteroatom bond is highlighted in the present invention by the spectroscopy analysis techniques commonly known and used by the person skilled in the art (proton, carbon, fluorine and boron NMR, mass spectrometry and IR spectrometry).

Compounds of Formula A or A'

The boron compounds comprising at least one hydroxy, amino or sulfhydryl group used in the preparation of the organometallic compounds according to the present invention can be described by general formulas A or A':

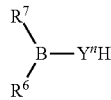

A

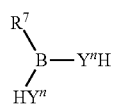

A' wherein:
$R^6$, $R^7$, identical, different or bonded, represent hydrocarbyl radicals having 1 to 30 carbon atoms, for example alkyl, cycloalkyi or aromatic, aryl or aralkyl groups, optionally substituted by hydroxyls, sulfhydryls or halogenides, $Y^n$, different or identical, n is equal to 1, 2, 3 or 4, $Y^1$, $Y^2$, $Y^3$, $Y^4$ representing an oxygen atom, a sulfur atom or a nitrogen atom, bonded to a hydrogen or a hydrocarbyl radical having 1 to 30 carbon atoms, for example alkyl, aryl or aralkyl groups, $R^6$, $R^7$, identical, different or bonded, can also represent hydrocarbyl radicals wherein one or more hydrogen atoms are replaced by halogenides or groups comprising at least one heteroelement such as oxygen, nitrogen, sulfur or silicon, $R^6$, $R^7$, identical, different or bonded, can also represent alkoxy, aryloxy or amidide groups, $R^6$, $R^7$ can be bonded to the $Y^n$ in cases where the $Y^n$ are amino groups, $R^6$, $R^7$ can have cationic groups such as ammoniums or phosphoniums, or anionic groups such as sulfates.

Preferably, $R^6$ and $R^7$ represent the mesityl or phenyl radicals.

Examples of boron compounds that can be used in the present invention are dimesitylborinic acid, diphenylborinic acid, 2,4,6-trifluoromethylphenylboronic acid, phenylboronic acid, mesitylboronic acid, pentafluorophenylborinic acid, phenylboronic acid ethalonamine ester, phenylboronic acid 2-hydroxyaniline ester.

The Transition Metal Compound of Formula B

According to the present invention, the compound of a group 6 transition metal of imido alkylidene type can be described by general formula B:

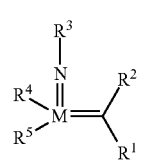

B

In this formula, M represents molybdenum or tungsten.

$R^1$ and $R^2$, identical or different, represent hydrogen, halogenides (F, Cl, Br, I), alkyl, cycloalkyl or aryl groups, optionally substituted, cyclopentadienyls, substituted or not (denoted by Cp), alkoxy, aryloxy, amidide, hydrido, carboxylate, oxalate, phosphonium or siloxane groups.

$R^3$ represents alkyl, cycloalkyl or aryl groups, optionally substituted, cyclopentadienyls, substituted or not (denoted by Cp).

Preferably, $R^3$ represents the 2,6-di-isopropylephenyi or adamantyl group.

$R^4$ and $R^5$, identical or different, represent hydrogens, halogenides (F, Cl, Br, I), alkyl, cycloalkyl or aryl groups, optionally substituted, cyclopentadienyls, substituted or not (denoted by Cp), alkoxy, aryloxy, amidide, hydrido, carboxylate, oxalate, β-diketiminate, iminopyrrolide, amidinate, pyrrolide groups, optionally substituted.

$R^1$, $R^2$, $R^3$, $R^4$ and $R^5$ can be bonded to one another so as to form one or more rings.

Preferably, $R^4$ and $R^5$ are 2,2-di(trifluoromethyl)propanoxy or 2,5-dimethylpyrrolide groups.

The compound of a group 6 transition metal of formula B can be of higher-order monomeric, dimeric or oligomeric nature.

The adducts of the compounds of formula B described above with a Lewis base can also be used according to the present invention. Examples of Lewis bases that can be used according to the present invention are ethers, amines, thioethers and phosphines.

Examples of compounds of formula B of a group 6 transition metal that can be used according to the present invention are Mo(N-2,6-iPr$_2$C$_6$H$_3$)(CHCMe$_2$Ph)(2,5-MeNC$_4$H$_2$)$_2$, Mo(N-2,6-iPr$_2$C$_6$H$_3$)(CHCMe$_2$Ph)(NC$_4$H$_2$)$_2$, Mo(N-2,6-iPr$_2$C$_6$H$_3$)(CHCMe$_2$Ph)(2,5-iPrNC$_4$H$_2$)$_2$, Mo(N-2,6-iPr$_2$C$_6$H$_3$)(CHCMe$_2$Ph)(2,5-PhNC$_4$H$_2$)$_2$, Mo(N-2,6-iPr$_2$C$_6$H$_3$)(CHCMe$_3$)(2,5-MeNC$_4$H$_2$)$_2$, Mo(N-2,6-iPr$_2$C$_6$H$_3$)(CHCMe$_3$)(NC$_4$H$_2$)$_2$, Mo(N-2,6-iPr$_2$C$_6$H$_3$)(CHCMe$_3$)(2,5-PhNC$_4$H$_2$)$_2$, Mo(N-2,6-iPr$_2$C$_6$H$_3$)(CHCMe$_3$)(2,5-PhNC$_4$H$_2$)$_2$, Mo(N-2,6-Me$_2$C$_6$H$_3$)(CHCMe$_2$Ph)(2,5-MeNC$_4$H$_2$)$_2$, Mo(N-2,6-Me$_2$C$_6$H$_3$)(CHCMe$_2$Ph)(NC$_4$H$_2$)$_2$, Mo(N-2,6-Me$_2$C$_6$H$_3$)(CHCMe$_2$Ph)(2,5-iPrNC$_4$H$_2$)$_2$, Mo(N-2,6-Me$_2$C$_6$H$_3$)(CHCMe$_2$Ph)(2,5-PhNC$_4$H$_2$)$_2$, Mo(N-2,6-Cl$_2$C$_6$H$_3$)(CHCMe$_2$Ph)(2,5-

MeNC$_4$H$_2$)$_2$, Mo(N-2,6-Cl$_2$C$_6$H$_3$)(CHCMe$_2$Ph)(NC$_4$H$_2$)$_2$, Mo(N-2,6-Cl$_2$C$_6$H$_3$)(CHCMe$_2$Ph)(2,5-iPrNC$_4$H$_2$)$_2$, Mo(N-2,6-Cl$_2$C$_6$H$_3$)(CHCMe$_2$Ph)(2,5-PhNC$_4$H$_2$)$_2$, Mo(N-Adamantyl)(CHCMe$_2$Ph)(2,5-MeNC$_4$H$_2$)$_2$, Mo(N-Adamantyl)(CHCMe$_2$Ph)(NC$_4$H$_2$)$_2$, Mo(N-Adamantyl)(CHCMe$_2$Ph)(2,5-iPrNC$_4$H$_2$)$_2$, Mo(N-Adamantyl)(CHCMe$_2$Ph)(2,5-PhNC$_4$H$_2$)$_2$, Mo(N-2,6-iPr$_2$C$_6$H$_3$)(CHCMe$_2$Ph)(OCMe(CF$_3$)$_2$)$_2$, Mo(N-2,6-iPr$_2$C$_6$H$_3$)(CHCMe$_2$Ph)(OTf)$_2$(dme), Mo(N-2,6-iPr$_2$C$_6$H$_3$)(CHCMe$_2$Ph)Cl$_2$(dme), Mo(N-2,6-iPr$_2$C$_6$H$_3$)(CHCMe$_2$Ph)(CH$_2$-$^t$Bu)$_2$, Mo(N-2,6-iPr$_2$C$_6$H$_3$)(CHCMe$_2$Ph)(CH$_2$—CMe$_2$Ph)$_2$, W(N-2,6-iPr$_2$C$_6$H$_3$)(CHCMe$_2$Ph)(2,5-MeNC$_4$H$_2$)$_2$, W(N-2,6-iPr$_2$C$_6$H$_3$)(CHCMe$_2$Ph)(NC$_4$H$_4$)$_2$, W(N-2,6-iPr$_2$C$_6$H$_3$)(CHCMe$_3$)(OCMe(CF$_3$)$_2$)$_2$, W(N-2,6-iPr$_2$C$_6$H$_3$)(CHCMe$_2$Ph)(OC$_6$F$_5$)$_2$)$_2$, W(N-2,6-iPr$_2$C$_6$H$_3$)(CHCMe$_3$)(OCMe(CF$_3$)$_2$)(NC$_4$H$_4$).

The adducts of these compounds with Lewis bases such as ethers, amines, thioethers or phosphines can also be used according to the present invention.

Organometallic Compounds of Formula I, II, III and IV

According to the present invention, the organometallic compounds described by general formulas I, II, III and IV, wherein M, R$^1$, R$^2$, R$^3$, R$^4$, R$^6$, R$^7$ and X$^1$, X$^2$, X$^3$, X$^4$, are defined as above.

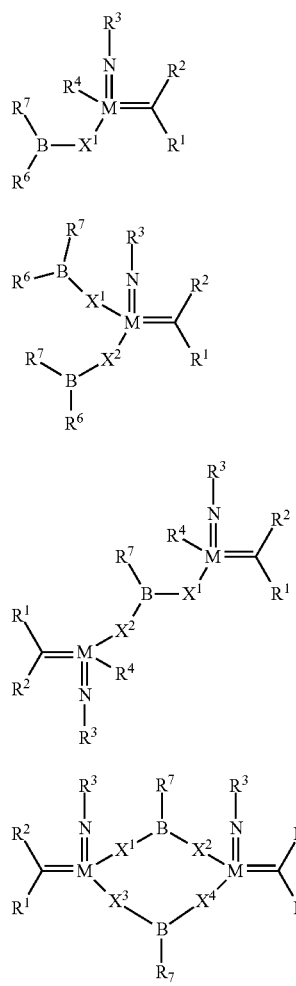

The adducts of the organometallic compounds supported on anions with a Lewis base can also be used according to the present invention.

Method of Synthesizing Organometallic Complexes I, II, III and IV

Synthesis of the group 6 organometallic compounds of general formula I, II, III and IV is carried out through the reaction of at least one boron compound of formula A or A' with a compound of a group 6 transition metal of imido alkylidene type of formula B.

The reaction can occur simply by contacting, followed by stirring, the compound of formula A or A' with the compound of formula B, optionally in the presence of a solvent. Addition of the various constituents can be done in any order.

The compounds of formula A or A' can also be activated by means of a base prior to reacting with the compound of formula B.

The molar ratio of the compound of formula A or A' with respect to the base can range between 0.1/1 and 100/1. Preferably, the molar ratio ranges between 0.1/1 and 10/1 more preferably between 1/1 and 2/1.

Bases likely to be used are notably n-butyllithium or sodium hydride.

Preferably, the reaction can be carried out through addition of the compound of formula A or A' to the compound of formula B in a solvent.

The solvent can be selected from the group of organic solvents or an ionic liquid and/or mixtures thereof. The organic solvents are preferably aprotic solvents. Examples of solvents that can be used in the synthesis method according to the present invention are hydrocarbons such as pentane, hexane, cyclohexane or heptane, aromatic hydrocarbons such as benzene, toluene or xylenes, chlorinated solvents such as dichloromethane, or acetone, acetonitrile, diethylether, THF, DMSO and DMF.

The molar ratio of the compound of formula A or A' to the compound of formula B can range between 0.1/1 and 100/1. Preferably, the molar ratio ranges between 0.5/1 and 10/1, and more preferably between 1/1 and 2/1.

The temperature of the reaction between the compound of formula A or A' and the compound of formula B ranges between −100° C. and 150° C., preferably between −78° C. and 50° C.

The compounds of formula I, II, III and IV can be isolated by means of the conventional methods used in coordination chemistry or organic synthesis, for example precipitation or crystallization in an organic solvent or a mixture of organic solvents.

The organometallic compounds described above are now described more precisely within the context of their use as a catalytic composition for an olefin metathesis method.

This catalytic composition comprises the following characteristic elements:
I) at least one organometallic compound of formula I, II, III or IV,
II) and optionally a solvent.

The catalytic system can also be generated <<in situ>> in the reactor. The catalytic composition then results from contacting the following characteristic elements:
I) at least one compound of formula A or A', optionally pretreated by a base,
II) at least one compound of formula B,
III) and optionally a solvent.

The solvent used in the catalytic compositions according to the present invention is also selected from the group of organic solvents and ionic liquids or mixtures thereof.

In the catalytic compositions according to the invention, the molar ratio of the compound of formula A or A' to the compound of formula B can range between 0.1/1 and 100/1.

Preferably, the molar ratio ranges between 0,5/1 and 10/1, and more preferably between 1/1 and 2/1.

The Olefin Metathesis Method

The olefin metathesis method according to the present invention optionally uses a solvent.

The solvent can be selected from the group of organic solvents and ionic liquids.

The organic solvent is preferably an aprotic solvent. Examples of solvents that can be used in the method of the present invention are hydrocarbons such as pentane, hexane, cyclohexane or heptane, aromatic hydrocarbons such as benzene, toluene or xylenes, chlorinated solvents such as dichloromethane, or acetone, acetonitrile, diethylether, THF, DMSO and DMF, The organic solvent is preferably a hydrocarbon or aromatic hydrocarbon solvent.

The ionic liquid preferably consists of a $Q^+$ cation as defined above, associated with an organic or inorganic anion. The $Q^+$ cation is preferably an organic cation. The anion is preferably selected from among the following anions: halogenides, nitrates, sulfates, alkylsulfates, phosphates, alkylphosphates, acetates, halogenoacetates, tetrafluoroborates, tetrachloroborates, hexafluorophosphates, trifluoro-tris-(pentafluoroethyl) phosphates, hexafluoroantimonates, fluorosulfonates, alkylsulfonates (for example methylsulfonate), perfluoroalkylsulfonates (for example trifluoromethylsulfonate), bis(perfluoroalkylsuifonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_2^-$, arenosulfonates, optionally substituted by halogen or halogenoalkyl groups, the tetraphenylborate anion and the tetraphenylborates anions whose aromatic rings are substituted, tetra-(trifluoroacetoxy)-borate, bis-(oxalato)-borate, dicyanamide and tricyanomethylide.

A mixture of organic solvents and/or of ionic liquids can be used for the olefin metathesis method according to the present invention.

The compounds that go into the catalytic composition according to the invention can be mixed in any order. Mixing can be done simply by contacting, followed by stirring, until a homogeneous liquid forms. Mixing can be achieved outside the olefin metathesis reactor or, preferably, in this reactor.

In the case of a gaseous reactant (such as ethylene for example), the reaction pressure can range between atmospheric pressure and 200 bars (20 MPa). Preferably, this pressure ranges between atmospheric pressure and 100 bars (10 MPa), and more preferably between atmospheric pressure and 30 bars (3 MPa). This gaseous reactant can be used pure or in admixture, or diluted with a paraffin (inert).

The reactions of the method according to the invention are catalysed by the catalytic composition described above, which can be added to the reaction medium as a solid, but it can also be added in solution when it is dissolved in a solvent.

Although the method according to the present invention can be applied to any olefin metathesis reaction, it is particularly useful for olefin homometathesis and cross metathesis.

According to the invention, the olefins considered in the olefin metathesis reaction con be linear, internal or terminal. More particularly, these olefins are selected from among ethylene, propylene, n-butenes and n-pentenes, n-hexenes, n-heptenes, n-octenes, n-nonenes or n-decenes, as found in <<cuts>> from oil refining processes, such as the Fischer-Tropsch process, or catalytic cracking or steam cracking.

According to the invention, the olefins considered in the olefin metathesis reaction can be functionalized. Preferably, the functionalized olefins are selected from any unsaturated fatty substance comprising at least one ethylenic insaturation, acrylonitrile, acrylic acid, methyl acrylate, but-3-enenitrile, but-3-enoic acid, methyl but-3-enoate.

The olefin metathesis reaction can be carried out in a closed system, a semi-open system or under continuous conditions, with one or more reaction stages. Vigorous stirring will provide good contact between the reactant(s) and the catalytic composition.

The reaction temperature can range between −40° C. and +250° C., preferably between 0° C. and +150° C.

The following examples illustrate the invention without limiting the scope thereof.

Abbreviations used in the Examples

Mes: 2,4,6-trimethylphenyl,

EXAMPLES

In the following examples, the conversion corresponds to the difference between the amount of material of the limiting reactant at the beginning of the reaction and the amount of material of the limiting reactant remaining at the end of the reaction, divided by the amount of material of the limiting reactant at the beginning of the reaction. This result is multiplied by one hundred so as to obtain a conversion in percentage.

$$\text{Conversion (\%)} = 100 * (n(\text{limiting reactant at } t_{initial}) - n(\text{limiting reactant at } t_{final})) / n(\text{limiting reactant at } t_{initial})$$

The selectivity, expressed in percentage, gives the amount of desired product formed in relation to the number of moles consumed of the limiting reactant.

$$\text{Selectivity (\%)} = n(\text{desired product}) / (n(\text{limiting reactant at } t_{initial}) - n(\text{limiting reactant at } t_{final}))$$

Example of Compounds of Formula A

The compound of type A used hereafter is the commercial product $(Mes)_2BOH$ (Sigma-Aldrich).

Example of Compounds of Formula B

The compound of type B used hereafter is the commercial complex $Mo(N-2,6-iPr_2C_6H_3)(CHCMe_2Ph)(2,5-MeNC_4H_2)_2$ (Strem Chemicals).

Example of Preparation of Compounds of Formula I

Example 1

Preparation of $Mo(N-2,6-Pr_2C_6H_3)(CHCMe_2Ph)(2,5-MeNC_4H_2)(OB(Mes)_2)$

The entire experiment is carried out under an argon atmosphere. All the reactants and the solvents are first degassed and conditioned under an argon atmosphere.

24 mg $Mo(N-2,6-iPr_2C_6H_3)(CHCMe_2Ph)(2,5-MeNC_4H_2)_2$ and 10 mg $(Mes)_2BOH$ are fed into a 30-ml Schlenk tube, provided with a magnetic stirrer, in a glove box. The two solids are dissolved in 1 ml dichloromethane and the solution is stirred for 1 hour at ambient temperature. The complex is used directly as a catalyst.

Compound $Mo(N-2,6-Pr_2C_6H_3)(CHCMe_2Ph)(2,5-MeNC_4H_2)OB(Mes)_2)$ is characterized by proton NMR.

RMN $^1H$ (300.1 MHz, $CD_2Cl_2$) (δ, ppm): 0.97 (m, 6H, $CH_3$); 1.13 (d, 6H, $^3J_{HH}$=7.1 Hz, $CH(CH_3)_2$); 1.53 (d, 6H, $^3J_{HH}$=7.1 Hz, $CH(CH_3)_2$); 2.20 (s, 6H, $CH_3$); 2.26 (s, 3H, CH₃); 2.27 (s, 3H, CH₃); 3.47 (sept, 2H, ³J_HH=7.1 Hz, CH(CH₃)₂); 5.72 (s, 2H, pyr), 6.76 (s, 4H, Ar); 7.10-7.25 (m, 8H, Ar); 11.43 (s, 1H,=CH).

Example of Olefin Metathesis Catalysis

Example 2

1-Octene Homometathesis Catalysed by Mo(N-2,6-Pr₂C₆H₃) (CHCMe₂Ph)(2,5-MeNC₄H₂)(OB(Mes)₂)

The entire experiment is carried out under an argon atmosphere. All the reactants and the solvents are first degassed and conditioned under an argon atmosphere.

996 mg 1-octene (Aldrich, O480-6) and 260 mg dodecane (VWR, 23,586-293 internal standard) are fed into a 30-ml Schlenk tube, provided with a magnetic stirrer. Stirring is achieved for 5 minutes, then 0.25 ml of the solution of complex Mo(N-2,6-Pr₂C₆H₃)(CHCMe₂Ph)(2,5-MeNC₄H₂)(OB (Mes)₂) (example 1) is added. The reaction is stirred for two hours at ambient temperature and in a dark place. Analysis of the products by gas chromatography shows that tetradecene, and ethylene that is not detected, have been formed. The conversion to 1-octene is 74%, The 3-hexene selectivity is 98%.

Example 3

2-pentene Homometathesis Catalysed by Mo(N-2,6-Pr₂C₆H₃) (CHCMe₂Ph)(2,5-MeNC₄H₂)(OB(Mes)₂)

The entire experiment is carried out under an argon atmosphere. All the reactants and the solvents are first degassed and conditioned under an argon atmosphere.

547 mg 2-pentene (Fluka, 14,377-4) and 240 mg dodecane (VWR, 23,586-293 internal standard) are fed into a 30-ml Schlenk tube, provided with a magnetic stirrer. Stirring is achieved for 5 minutes, then 0.25 ml of the solution of complex Mo(N-2,6-Pr₂C₆H₃)(CHCMe₂Ph)(2,5-MeNC₄H₂)(OB (Mes)₂) (example 1) is added. The reaction is stirred for two hours at ambient temperature and in a dark place. Analysis of the products by gas chromatography shows that 3-hexene and 2-butene have been formed. The conversion to 2-pentene is 22% and the 3-hexene selectivity is 73%.

The invention claimed is:

1. An organometallic compound based on a group 6 metal, of imido alkylidene type, comprising at least one boron-based ligand, bonded to the metal via a covalent bond with sulfur, oxygen or nitrogen, which is one of the following formulas I, II, III or IV:

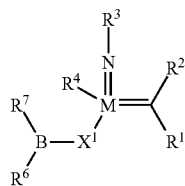

I

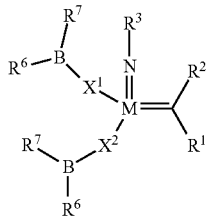

II

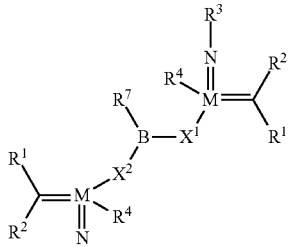

III

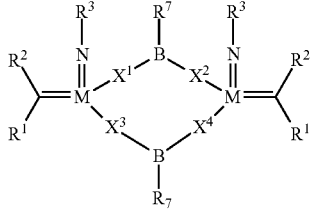

IV wherein:

M represents molybdenum or tungsten,

X¹, X², X³, and X⁴, different or identical, each represents an oxygen atom, a sulfur atom or a NH group, optionally substituted by a hydrocarbyl radical having 1 to 30 carbon atoms, R¹, R², R³ and R⁴, identical or different, each represents hydrogen, a halogenide or an organic radical having 1 to 30 carbon atoms, and R⁶ and R⁷, identical or different, each represents an organic radical having 1 to 30 carbon atoms.

2. A compound as claimed in claim 1, wherein

R⁶ and R⁷, identical or different, each represents an alkyl, cycloalkyl, aryl or aralkyl radical, which is optionally substituted, a hydrocarbyl radicals wherein one or more hydrogen atoms are each replaced by a halogenide or a group comprising at least one oxygen, nitrogen, sulfur or silicon atom, or an alkoxy, aryloxy or amide group, and R¹, R², R³ and R⁴ each represents an alkyl, cycloalkyl or aryl group, which is optionally substituted, a cyclopentadienyl group, which is substituted or not, or an alkoxy, aryloxy, amide, hydrido, carboxylate, oxalate, β-diketiminate, iminopyrrolide, amidinate or boratabenzene group.

3. A mixture of group 6 organometallic compounds of imido alkylidene type, comprising at least one boron-based ligand, bonded to the metal via a covalent bond with a sulfur, oxygen or nitrogen, obtained by reaction between at least one boron compound comprising at least one hydroxy, amino or sulfhydryl function, of formula A or A', with at least one compound of a group 6 transition metal of imido alkylidene type of formula B, optionally in the presence of a solvent, formulas A and A' being:

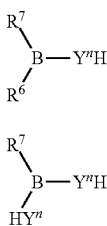

A A' wherein
Y, identical or different, each represents an oxygen atom, a sulfur atom or a nitrogen atom, bonded to a hydrogen or a hydrocarbyl radical having 1 to 30 carbon atoms,
$R^6$, $R^7$, identical or different, each represents an organic radical having 1 to 30 carbon atoms,
formula B being:

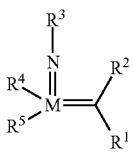

wherein
M represents molybdenum or tungsten, and
$R^1$, $R^2$, $R^3$, $R^4$ and $R^5$, identical or different, each represents an organic radical, hydrogen or a halogenide.

4. A mixture as claimed in claim 3, wherein
the compound of formula A or A' is dimesitylborinic acid, diphenylborinic acid, 2,4,6-trifluoromethylphenylboronic acid, phenylboronic acid, mesitylboronic acid, pentafluorophenylborinic acid, phenylboronic acid ethalonamine ester, or phenylboronic acid 2-hydroxyaniline ester, and
the compound of formula B is Mo(N-2,6-iPr$_2$C$_6$H$_3$)(CHCMe$_2$Ph)(2,5-Me$_2$NC$_4$H$_2$)$_2$, Mo(N-2,6-iPr$_2$C$_6$H$_3$)(CHCMe$_2$Ph)(NC$_4$H$_2$)$_2$, Mo(N-2,6-iPr$_2$C$_6$H$_3$)(CHCMe$_2$Ph)(2,5-iPrNC$_4$H$_2$)$_2$, Mo(N-2,6-iPr$_2$C$_6$H$_3$)(CHCMe$_2$Ph)(2,5-PhNC$_4$H$_2$)$_2$, Mo(N-2,6-iPr$_2$C$_6$H$_3$)(CHCMe$_3$)(2,5-Me$_2$NC$_4$H$_2$)$_2$, Mo(N-2,6-iPr$_2$C$_6$H$_3$)(CHCMe$_3$)(NC$_4$H$_2$)$_2$, Mo(N-2,6-iPr$_2$C$_6$H$_3$)(CHCMe$_3$)(2,5-PhNC$_4$H$_2$)$_2$, Mo(N-2,6-iPr$_2$C$_6$H$_3$)(CHCMe$_3$)(2,5-PhNC$_4$H$_2$)$_2$, Mo(N-2,6-Me$_2$C$_6$H$_3$)(CHCMe$_2$Ph)(2,5-Me$_2$NC$_4$H$_2$)$_2$, Mo(N-2,6-Me$_2$C$_6$H$_3$)(CHCMe$_2$Ph)(NC$_4$H$_2$)$_2$, Mo(N-2,6-Me$_2$C$_6$H$_3$)(CHCMe$_2$Ph)(2,5-iPrNC$_4$H$_2$)$_2$, Mo(N-2,6-Me$_2$C$_6$H$_3$)(CHCMe$_2$Ph)(2,5-PhNC$_4$H$_2$)$_2$, Mo(N-2,6-Cl$_2$C$_6$H$_3$)(CHCMe$_2$Ph)(2,5-Me$_2$NC$_4$H$_2$)$_2$, Mo(N-2,6-Cl$_2$C$_6$H$_3$)(CHCMe$_2$Ph)(NC$_4$H$_2$)$_2$, Mo(N-2,6-Cl$_2$C$_6$H$_3$)(CHCMe$_2$Ph)(2,5-iPrNC$_4$H$_2$)$_2$, Mo(N-2,6-Cl$_2$C$_6$H$_3$)(CHCMe$_2$Ph)(2,5-PhNC$_4$H$_2$)$_2$, Mo(N-Adamantyl)(CHCMe$_2$Ph)(2,5-Me$_2$NC$_4$H$_2$)$_2$, Mo(N-Adamantyl)(CHCMe$_2$Ph)(NC$_4$H$_2$)$_2$, Mo(N-Adamantyl)(CHCMe$_2$Ph)(2,5-iPrNC$_4$H$_2$)$_2$, Mo(N-Adamantyl)(CHCMe$_2$Ph)(2,5-PhNC$_4$H$_2$)$_2$, Mo(N-2,6-iPr$_2$C$_6$H$_3$)(CHCMe$_2$Ph)(OCMe(CF$_3$)$_2$)$_2$, Mo(N-2,6-iPr$_2$C$_6$H$_3$)(CHCMe$_2$Ph)(OC$_6$F$_5$)$_2$)$_2$, Mo(N-2,6iPr$_2$C$_6$H$_3$)(CHCMe$_3$)(OCMe(CF$_3$)$_2$)$_2$, Mo(N-2,6-iPr$_2$C$_6$H$_3$)(CHCMe$_2$Ph)(OTf)$_2$(dme), Mo(N-2,6-iPr$_2$C$_6$H$_3$)(CHCMe$_2$Ph)Cl$_2$(dme), Mo(N-2,6-iPr$_2$C$_6$H$_3$)(CHCMe$_2$Ph)(CH$_2$-$^t$Bu)$_2$, Mo(N-2,6-iPr$_2$C$_6$H$_3$)(CHCMe$_2$Ph)(CH$_2$-CMe$_2$Ph)$_2$, W(N-2,6-iPr$_2$C$_6$H$_3$)(CHCMe$_2$Ph)(2,5-Me$_2$NC$_4$H$_2$)$_2$, W(N-2,6-iPr$_2$C$_6$H$_3$)(CHCMe$_2$Ph)(NC$_4$H$_4$)$_2$, W(N-2,6-iPr$_2$C$_6$H$_3$)(CHCMe$_3$)(OCMe(CF$_3$)$_2$)$_2$, W(N-2,6-iPr$_2$C$_6$H$_3$)(CHCMe$_2$Ph)(OC$_6$F$_5$)$_2$)$_2$, or W(N-2,6-iPr$_2$C$_6$H$_3$)(CHCMe$_3$)(OCMe(CF$_3$)$_2$)(NC$_4$H$_4$).

5. A method for synthesis of a compound as claimed in claim 1, comprising reacting a compound of formula A or A', optionally activated by a base, with a compound of formula B of a group 6 transition metal of imido alkylidene type, optionally in the presence of a solvent,
formulas A and A' being:

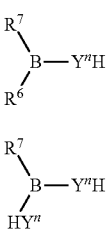

wherein
Y, identical or different, each represents an oxygen atom, a sulfur atom or a nitrogen atom, bonded to a hydrogen or a hydrocarbyl radical having 1 to 30 carbon atoms,
$R^6$, $R^7$, identical or different, each represents an organic radical having 1 to 30 carbon atoms,
and the compound of formula B being:

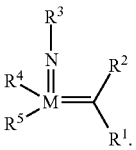

wherein
M represents molybdenum or tungsten, and
$R^1$, $R^2$, $R^3$, $R^4$ and $R^5$, identical or different, each represents an organic radical, hydrogen or a halogenide.

6. A method as claimed in claim 5, wherein the solvent is an organic solvent, an ionic liquid, or a mixture thereof.

7. A method as claimed in claim 5, wherein the molar ratio of the compound of formula A or A' to the compound of formula B is between 0.1/1 and 100/1.

8. A method as claimed in claim 5, wherein the reaction is carried out at a temperature between −100° C. and 150° C.

9. A catalytic composition comprising:
i) at least one compound of formula I, II, III or IV

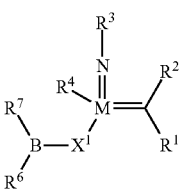

-continued

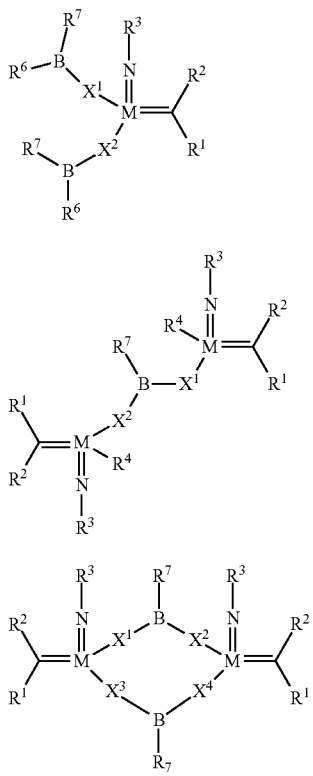

wherein:
M represents molybdenum or tungsten,
R¹, R², R³ and R⁴, identical or different, each represents hydrogen, a halogenide or an organic radical having 1 to 30 carbon atoms,
R⁶ and R⁷, identical or different, each represents an organic radical having 1 to 30 carbon atoms, and
X¹, X², X³, and X⁴, different or identical, each represents an oxygen atom, a sulfur atom or a NH group, optionally substituted by a hydrocarbyl radical having 1 to 30 carbon atoms,
ii) at least one catalytically acceptable carrier,
iii) and optionally a solvent.

10. A catalytic composition resulting from contacting:
i) at least one boron compound comprising at least one hydroxy, amino or sulfhydryl function of formula A or A', optionally activated by a base,
formulas A and A' being:

$$\begin{array}{c} R^7 \\ \diagdown \\ B-Y^nH \\ \diagup \\ R^6 \end{array} \quad A$$

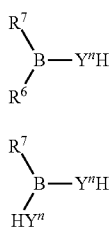

wherein
Y, identical or different, each represents an oxygen atom, a sulfur atom or a nitrogen atom, bonded to a hydrogen or a hydrocarbyl radical having 1 to 30 carbon atoms,
R⁶, R⁷, identical or different, each represents an organic radical having 1 to 30 carbon atoms,
ii) at least one compound of a group 6 transition metal of imido alkylidene type of formula B:

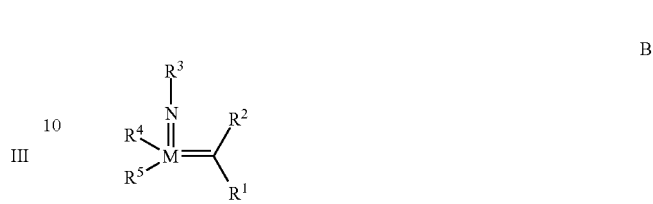

wherein
M represents molybdenum or tungsten, and
R¹, R², R³, R⁴ and R⁵, identical or different, each represents an organic radical, hydrogen or a halogenide,
iii) at least one catalytically acceptable carrier,
iv) and optionally a solvent.

11. A catalytic composition as claimed in claim 9, wherein the solvent is an organic solvent, ionic liquid, or a mixture thereof.

12. A catalytic composition as claimed in claim 9, wherein the molar ratio of the compound of formula A or A' to the compound of formula B is between 0.1/1 and 100/1.

13. An olefin metathesis method, comprising performing the olefin metathesis through a catalytic reaction by a catalytic composition as claimed in claim 9.

14. A method as claimed in claim 13, wherein the reaction is carried out at a temperature between −40° C. and 250° C., and at a pressure between atmospheric pressure and 20 MPa.

15. A method as claimed in claim 13, wherein the olefin metathesis is performed on an olefin that is selected from the group consisting of n-butene, n-pentene, n-hexene, n-heptene, n-octene, an alkyl oleate, or a mixture thereof, in pure form or diluted by an alkane, or as found in a cut from an oil refining process, or a vegetable oil.

16. A compound as claimed in claim 1, which is of formula I.

17. A compound as claimed in claim 1, which is of formula II.

18. A compound as claimed in claim 1, which is of formula III.

19. A compound as claimed in claim 1, which is of formula IV.

20. A mixture as claimed in claim 3, wherein
the compound of formula A or A' is dimesitylborinic acid, diphenylborinic acid, 2,4,6-trifluoromethylphenylboronic acid, phenylboronic acid, mesitylboronic acid, pentafluorophenylborinic acid, phenylboronic acid ethalonamine ester, or phenylboronic acid 2-hydroxyaniline ester, and
the compound of formula B is Mo(N-2,6-iPr₂C₆H₃)(CHCMe₂Ph)(NC₄H₂)₂, Mo(N-2,6-iPr₂C₆H₃)(CHCMe₂Ph)(2,5-iPrNC₄H₂)₂, Mo(N-2,6-iPr₂C₆H₃)(CHCMe₂Ph)(2,5-PhNC₄H₂)₂, Mo(N-2,6-iPr₂C₆H₃)(CHCMe₃)(NC₄H₂)₂, Mo(N-2,6-iPr₂C₆H₃)(CHCMe₃)(2,5-PhNC₄H₂)₂, Mo(N-2,6-iPr₂C₆H₃) (CHCMe₃)(2,5-PhNC₄H₂)₂, Mo(N-2,6-Me₂C₆H₃)(CHCMe₂Ph)(NC₄H₂)₂, Mo(N-2,6-Me₂C₆H₃)(CHCMe₂Ph)(2,5-iPrNC₄H₂)₂, Mo(N-2,6-Me₂C₆H₃)(CHCMe₂Ph)(2,5-PhNC₄H₂)₂, Mo(N-2,6-Cl₂C₆H₃)(CHCMe₂Ph)(NC₄H₂)₂, Mo(N-2,6-Cl₂C₆H₃)(CHCMe₂Ph)(2,5-iPrNC₄H₂)₂, Mo(N-2,6-Cl₂C₆H₃)(CHCMe₂Ph)(2,5-PhNC₄H₂)₂, Mo(N-Adamantyl)(CHCMe₂Ph)(NC₄H₂)₂, Mo(N-Adamantyl) (CHCMe₂Ph)(2,5- iPrNC$_4$H$_2$)$_2$, Mo(N-Adamantyl)(CHCMe$_2$Ph)(2,5-PhNC$_4$H$_2$)$_2$, Mo(N-2,6-iPr$_2$C$_6$H$_3$)(CHCMe$_2$Ph)(OCMe(CF$_3$)$_2$)$_2$, Mo(N-2,6-iPr$_2$C$_6$H$_3$)(CHCMe$_2$Ph)(OC$_6$F$_5$)$_2$)$_2$, Mo(N-2,6-iPr$_2$C$_6$H$_3$)(CHCMe$_3$)(OCMe(CF$_3$)$_2$)$_2$, Mo(N-2,6-iPr$_2$C$_6$H$_3$)(CHCMe$_2$Ph)(OTf)$_2$(dme), Mo(N-2,6-iPr$_2$C$_6$H$_3$)(CHCMe$_2$Ph)Cl$_2$(dme), Mo(N-2,6-iPr$_2$C$_6$H$_3$)(CHCMe$_2$Ph)(CH$_2$-$^t$Bu)$_2$, Mo(N-2,6-iPr$_2$C$_6$H$_3$)(CHCMe$_2$Ph)(CH$_2$—CMe$_2$Ph)$_2$, W(N-2,6-iPr$_2$C$_6$H$_3$)(CHCMe$_2$Ph)(NC$_4$H$_4$)$_2$, W(N-2,6-iPr$_2$C$_6$H$_3$)(CHCMe$_3$) (OCMe(CF$_3$)$_2$)$_2$, W(N-2,6-iPr$_2$C$_6$H$_3$)(CHCMe$_2$Ph)(OC$_6$F$_5$)$_2$)$_2$, or W(N-2,6-iPr$_2$C$_6$H$_3$)(CHCMe$_3$) (OCMe(CF$_3$)$_2$)(NC$_4$H$_4$).

* * * * *

UNITED STATES PATENT AND TRADEMARK OFFICE
CERTIFICATE OF CORRECTION

PATENT NO. : 8,680,306 B2
APPLICATION NO. : 12/911973
DATED : March 25, 2014
INVENTOR(S) : Chahen et al.

It is certified that error appears in the above-identified patent and that said Letters Patent is hereby corrected as shown below:

In the Claims:

Column 11, lines 2-14 read

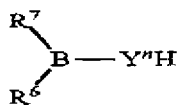

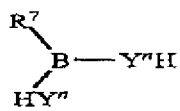

" A A' "

Should read --

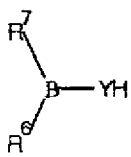 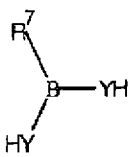

A        A'

Column 12, lines 15-24 read

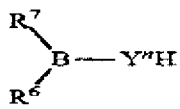

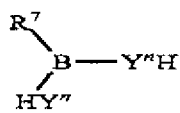

" A A' "

Signed and Sealed this
Nineteenth Day of August, 2014

Michelle K. Lee
*Deputy Director of the United States Patent and Trademark Office*

CERTIFICATE OF CORRECTION (continued)
U.S. Pat. No. 8,680,306 B2

Should read --

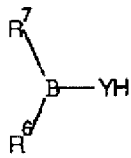 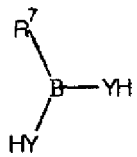

A        A'

Column 13, lines 51-63 read

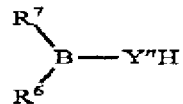

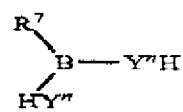

" A A' "

Should read --

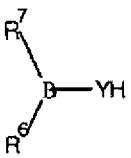 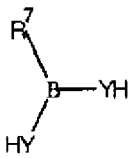

A        A'